United States Patent [19]

Kaneko et al.

[11] Patent Number: 5,646,317
[45] Date of Patent: Jul. 8, 1997

[54] PROCESSES FOR THE PREPARATION OF N-(LONG-CHAIN ACYL)AMINO ACID AND SALT THEREOF, AND INTERMEDIATE AMIDONITRILE AND PROCESS FOR THE PREPARATION THEREOF

[75] Inventors: Youhei Kaneko; Kohshiro Sotoya, both of Wakayama, Japan

[73] Assignee: Kao Corporation, Tokyo, Japan

[21] Appl. No.: 325,025

[22] Filed: Oct. 18, 1994

[30] Foreign Application Priority Data

Oct. 25, 1993 [JP] Japan .................... 5-266166

[51] Int. Cl.$^6$ ........................... C07C 231/00
[52] U.S. Cl. .................. 554/69; 54/54; 54/68
[58] Field of Search ............... 554/54, 68, 69

[56] References Cited

U.S. PATENT DOCUMENTS

| Re. 29,369 | 8/1977 | Fujimoto et al. | 554/69 |
|---|---|---|---|
| 2,927,126 | 3/1960 | Pursglove | 554/69 |

FOREIGN PATENT DOCUMENTS

| 1554477 | 1/1969 | France . |
| 4321656 | 11/1992 | Japan . |
| 0597787 | 4/1993 | Japan . |

OTHER PUBLICATIONS

"N–Lauroylsarcosine, Synthesis of N–Lauroylsarcosine Studies of Amino Acids III," Japanese Article By Tadashi Shirai et al. with English Abstract (Book Title) *Yuki Gosei Kagaku*, 1972.
Ind. Eng. Chem., vol. 50, pp. 1115–1118, "Continuous High Pressure Synthesis of 3–Aminopropionitrile", Smolin and Beegle., 1958.
J.A.S.C. vol. 169, pp. 844–846, "An Improved Synthesis of β–Alanine. III. The Addition of Ammonia to Acrylonitrile at 50–150°[1]", Ford et al., 1947.
Chemical Abstract, vol. 79, No. 25, Dec. 24, 1973, Col. OH, US; Shirai, Tadashi et al., "Imidazolines from alpha–acylamino nitriles".
Justus Liebigs Ann. Chem. (1972), 764, 69–93 Coden: JLACBF, 1972 Kurtz, Peter et al. "Enamides" p. 83 ¶ 7.
J. Zabicky "The Chemistry of Amides", 1970, Interscience Publishers, London. p. 73 and 96–105.

Chemical Abstracts, vol. 77, No. 5, 31 Jul. 1972, Col. OH, US; Shirai, Tadashi et al. "Amino acids. III. Synthesis of N–lauroylsarcosine".
Chemical Abstracts, vol. 133, No. 19, abstract of DE–3,835, 741,171690 1990.
Chemical abstracts, vol. 77, 1972, 18873.

*Primary Examiner*—Deborah D. Carr
*Attorney, Agent, or Firm*—Birch, Stewart, Kolasch & Birch, LLP

[57] ABSTRACT

To provide processes suitable for industrial production by which high-purity N-(long-chain acyl)amino acid and salt thereof can be prepared from inexpensive raw materials.

An alkyl ester of a fatty acid (2) is reacted with an aminonitrile (3) in the presence of a basic catalyst to form an amidonitrile (1), the amidonitrile (1) is hydrolyzed into an N-(long-chain acyl)amino acid salt (4) in the presence of a basic substance, the pH of the resulting aqueous solution is adjusted to a pH from 1 to 5 with a mineral acid to form an N-(long-chain acyl)amino acid (5), and this amino acid is recovered.

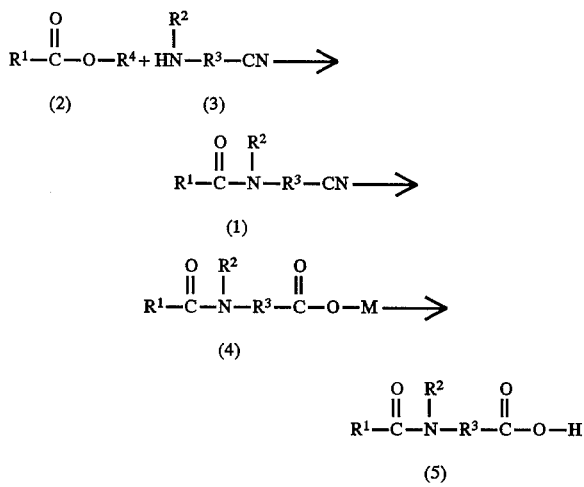

wherein $R^1CO-$ represents a fatty acid residue having 8 to 22 carbon atoms; $R^2$ represents a hydrogen atom or an alkyl group having 1 to 3 carbon atoms; $R^3$ represents an alkylene group having 1 to 5 carbon atoms; $R^4$ represents an alkyl group having 1 to 4 carbon atoms; and M represents a monovalent cation.

11 Claims, No Drawings

PROCESSES FOR THE PREPARATION OF N-(LONG-CHAIN ACYL)AMINO ACID AND SALT THEREOF, AND INTERMEDIATE AMIDONITRILE AND PROCESS FOR THE PREPARATION THEREOF

BACKGROUND OF THE INVENTION

1. Field of the Invention

The present invention relates to a process for the preparation of an N-(long-chain acyl)amino acid and a process for the preparation of a salt of an N-(long-chain acyl)amino acid, and an intermediate amidonitrile and a process for the preparation thereof. More particularly, the present invention relates to a process suitable for industrial production by which an amidonitrile, N-(long-chain acyl)amino acid or a salt thereof each having a high purity can be prepared from inexpensive raw materials through simple and easy operation independently of the material of the reactor used.

2. Description of the Related Art

N-(Long-chain acyl)amino acids and salts thereof are used in various fields, because they are excellent in surface activating effect and bacteriostatic activity and are low in irritant effects.

As a process for the preparation of an N-(long-chain acyl)amino acid salt, there has hitherto been known the Schotten-Baumann reaction which comprises reacting an amino acid with a fatty acid halide in the presence of an alkali, and further several improvements of the reaction have also been proposed. Furthermore, there has also been known a reaction of converting the salt prepared by the above reaction into an N-(long-chain acyl)amino acid through double decomposition with a strong acid.

These reactions are represented by the following reaction scheme:

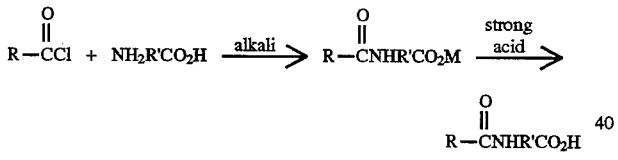

wherein RCO— represents a long-chain acyl group; and R' represents an alkylene group having 1 to 5 carbon atoms.

However, the Schotten-Baumann reaction and the improvements thereof must use, as the raw materials, an amino acid and a fatty acid halide, which are too expensive for industrial use. Further, the use of a fatty acid halide limits the material of the preparation apparatus used.

It has also been known that the quality of a fatty acid halide greatly influences the quality of the N-(long-chain acyl)amino acid prepared therefrom [see Japanese Patent Publication-A Nos. 4-321656 (published on Nov. 11, 1992) and 5-97787 (published on Apr. 20, 1993)]. Therefore, the preparation of an N-(long-chain acyl)amino acid or salt thereof each having a high quality necessitates complicated steps, disadvantageously.

Meanwhile, Shirai et al. disclosed a process for the preparation of an N-(long-chain acyl)amino acid or a salt thereof which comprises acylating an aminonitrile with an acid chloride and then hydrolyzing the obtained product [see Yuki Gosei Kagaku (Organic Synthetic Chemistry), Vol. 30, No. 1, p.p. 68–75, 1972].

However, the process of Shirai et al. also uses an acid chloride as the raw material, so that it must have disadvantages similar to those of the above Schotten Baumann reaction and improvements thereof.

Under these circumstances, it is advantageous to develop a process suitable for industrial production for preparing an N-(long-chain acyl)amino acid or a salt thereof.

DISCLOSURE OF THE INVENTION

SUMMARY OF THE INVENTION

The present invention aims at providing a process suitable for industrial production by which an N-(long-chain acyl) amino acid or salt thereof each having a high purity can be prepared from inexpensive raw materials; and an intermediate amidonitrile used in the process and a process for the preparation thereof.

The present inventors have made extensive studies on the preparation of the objective compound using an inexpensive aminonitrile as the raw material instead of an amino acid. As a result of the studies, they have found that the above object can be attained by selecting specific reaction conditions, though it involves a two-stage reaction as will be described below. The present invention has been accomplished on the basis of this finding.

Thus, the present invention relates to an intermediate amidonitrile and a process for the preparation thereof; and processes for the preparation of an N-(long-chain acyl) amino acid and a salt thereof, more precisely to the following items 1) to 10):

1) an amidonitrile represented by the formula (1'):

wherein $R^1CO$— represents a saturated or unsaturated fatty acid residue having 8 to 22 carbon atoms; $R^2$ represents a hydrogen atom or a linear or branched alkyl group having 1 to 3 carbon atoms; and $R^{3'}$ represents a linear or branched alkylene group having 2 to 5 carbon atoms;

2) a process for the preparation of an amidonitrile represented by the following formula (1):

wherein $R^1CO$— and $R^2$ are each as defined above; and $R^3$ represents a linear or branched alkylene group having 1 to 5 carbon atoms, which comprises a step of reacting a lower alkyl ester of a fatty acid represented by the formula (2):

(wherein $R^1CO$— is as defined above; and $R^4$ represents an alkyl group having 1 to 4 carbon atoms) with an aminonitrile represented by the formula

(wherein $R^2$ and $R^3$ are each as defined above) in the presence of a basic catalyst;

3) a process for the preparation of an amidonitrile as set forth in the above item 2), which comprises reacting a lower alkyl ester of a fatty acid represented by the above formula (2) with an aminonitrile represented by the above formula (3) in the presence of a basic catalyst, removing the basic catalyst from the reaction mixture, and then purifying the reaction product by distillation;

4) a process for the preparation of an amidonitrile as set forth in the above item 2), wherein the reaction of a lower alkyl ester of a fatty acid represented by the above formula (2) with an aminonitrile represented by the above formula (3) is conducted in the presence of an inert gas under an elevated pressure;

5) a process for the preparation of an amidonitrile as set forth in the above item 2), wherein the reaction of a lower alkyl ester of a fatty acid represented by the above formula (2) with an aminonitrile represented by the above formula (3) is conducted in the presence of a lower alcohol;

6) a process for the preparation of an amidonitrile as set forth in the above item 2), which further comprises the step of adding a lower alcohol before or during the reaction;

7) a process for the preparation of an N-(long-chain acyl) amino acid salt represented by the following formula (4):

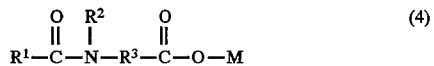

wherein $R^1CO-$, $R^2$ and $R^3$ are each as defined above; and M represents a monovalent cation, which comprises a step of hydrolyzing an amidonitrile represented by the formula (1):

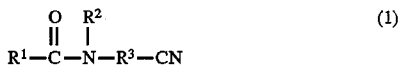

(wherein $R^1CO-$, $R^2$ and $R^3$ are each as defined above) in the presence of a basic substance;

8) a process for the preparation of an N-(long-chain acyl) amino acid represented by the following formula (5):

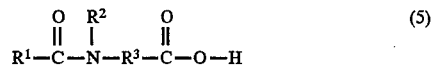

wherein $R^1CO-$, $R^2$ and $R^3$ are each as defined above, which comprises steps of adjusting the pH of the aqueous solution of an N-(long-chain acyl)amino acid salt represented by the formula (4):

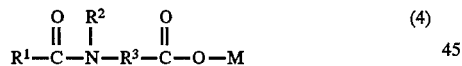

(wherein $R^1CO-$, $R^2$, $R^3$ and M are each as defined above), which has been prepared by the process as set forth in the above item 7), to a pH from 1 to 5 with a mineral acid, and then separating and recovering an N-(long-chain acyl)amino acid;

9) a process for the preparation of an N-(long-chain acyl) amino acid salt represented by the following formula (4):

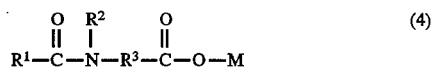

wherein $R^1CO-$, $R^2$, $R^3$ and M are each as defined above, which comprises steps of reacting a lower alkyl ester of a fatty acid represented by the formula (2):

(wherein $R^1CO-$ and $R^4$ are each as defined above) with an aminonitrile represented by the formula (3):

(wherein $R^2$ and $R^3$ are each as defined above) in the presence of a basic catalyst to form an amidonitrile represented by the formula (1):

(wherein $R^1CO-$ $R^2$ and $R^3$ are each as defined above), and then hydrolyzing the amidonitrile obtained in the presence of a basic substance; and 10) a process for the preparation of an N-(long-chain acyl) amino acid represented by the following formula (5):

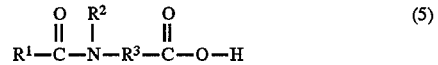

wherein $R^1CO-$, $R^2$ and $R^3$ are each as defined above, which comprises steps of reacting a lower alkyl ester of a fatty acid represented by the formula (2):

(wherein $R^1CO-$ and $R^4$ are each as defined above) with an aminonitrile represented by the formula (3):

(wherein $R^2$ and $R^3$ are each as defined above) in the presence of a basic catalyst to form an amidonitrile represented by the formula (1):

(wherein $R^1CO-$, $R^2$ and $R^3$ are each as defined above), hydrolyzing the amidonitrile obtained into an N-(long-chain acyl)amino acid salt represented by the formula (4):

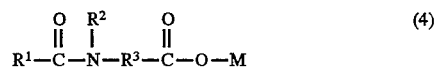

(wherein $R^1CO-$, $R^2$, $R^3$ and M are each as defined above) in the presence of a basic substance, adjusting the pH of the aqueous solution of the N-(long-chain acyl)-amino acid salt obtained to a pH from 1 to 5 with a mineral acid to form an N-(long-chain acyl)amino acid, and then separating and recovering the N-(long-chain acyl)amino acid.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Now, the reactions according to the present invention will each be described in detail.

a) Preparation Process for Amidonitrile

An amidonitrile represented by the formula (1) can be prepared by reacting a lower alkyl ester of a fatty acid represented by the formula (2) with an aminonitrile represented by the formula (3) in the presence of a basic catalyst.

The lower alkyl ester of a fatty acid represented by the formula (2) may be any lower alkyl (wherein the alkyl group has 1 to 4 carbon atoms) ester of a saturated or unsaturated, linear or branched fatty acid having 8 to 22 carbon atoms, preferably 12 to 18 carbon atoms. Specific examples thereof include methyl, ethyl and butyl esters of single fatty acids such as lauric acid, palmitic acid, stearic acid and oleic acid; and those of mixed fatty acids such as coconut oil fatty acid and beef tallow fatty acid, among which methyl esters of the fatty acids described above, such as methyl laurate, methyl stearate and methyl ester of beef tallow fatty acid, are preferable.

In the formula (3), $R^2$ is a hydrogen atom or a linear or branched alkyl group having 1 to 3 carbon atoms; and $R^3$ is a linear or branched alkylene group having 1 to 5 carbon atoms. It is preferable that $R^2$ be a hydrogen atom or a methyl group and $R^3$ be an ethylene group.

Specific examples of the aminonitrile represented by the formula (3) include $H_2NCH_2CN$,

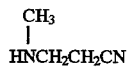

and $H_2NCH_2CH_2CN$, among which $H_2NCH_2CH_2CN$ is still preferable.

Although the aminonitrile may be one prepared by any process, $H_2NCH_2CH_2CN$, for example, can be prepared at a low cost from ammonia and acrylonitrile [see J. H. Ford, et al., J.A.C.S., 69, 844 (1947) and E. M. Smolin, et al., Ind. Eng. Chem., 50, 1115 (1958)].

Although the basic catalyst to be used in this reaction may be any one exhibiting basic properties, it is preferable in respect of handling and cost that the catalyst be an alkali metal or alkaline earth metal alcoholate having 1 to 3 carbon atoms, particularly sodium methylate or sodium ethylate.

Although the amount of the basic catalyst to be used in the preparation of the amidonitrile represented by the formula (1) is not particularly limited, it is preferably 1 to 20 mole % based on the amount of the aminonitrile represented by the formula (3). When the amount of the basic catalyst is less than 1 mole %, the reaction will take too long a time to be carried out industrially efficiently, while when it exceeds 20 mole %, the reaction time will not be shortened appreciably and the cost of the excess catalyst is uneconomical.

The reaction temperature of the amidation preferably ranges from 50° to 120° C. When the reaction temperature is lower than 50° C., the reaction rate will be too slow to be practical. In contrast, when the temperature is higher than 120° C., the amidonitrile formed will be decomposed into a fatty acid amide as a by-product, resulting in a lowered yield, though the reaction proceeds at a high rate. When the product of the amidation has such a high melting point that it will be solidified in the reaction system, it is preferable to use an appropriate amount of a solvent, such as methanol, ethanol, toluene, xylylene, N,N-dimethyl-formamide and dimethyl sulfoxide.

Although the prepared amidonitrile represented by the formula (1) can as such be used as the raw material of various reactions, it is preferable that the amidonitrile be purified by distillation, recrystallization or the like prior to use, because the amidonitrile prepared above is discolored. Generally, recrystallization is conducted by the use of equipment such as a filter and a dryer, and necessitates equipment for the recovery of the solvent used, thus being unfavorable as an industrial purification means. Accordingly, distillation is preferable.

When the reaction mixture containing the basic catalyst and the amldonitrile is as such distilled, most of the amidonitrile is converted into a fatty acid amide during the distillation resulting in a recovery of as low as about 10%. The term "recovery" used in this specification refers to a ratio of the amount of the amidonitrile contained in the distillate to that of the amidonitrile contained in the reaction mixture before the distillation. Accordingly, it is preferable that the reaction mixture be separated from the basic catalyst prior to the distillation.

For the removal of the basic catalyst from the reaction mixture, it is particularly preferable to employ a process which comprises neutralizing the basic catalyst with a mineral acid and filtering out the formed inorganic salt, or a process which comprises neutralizing the basic catalyst and centrifuging the resulting mixture to recover a catalyst-free reaction mixture. Examples of the mineral acid to be used in the above neutralization include hydrochloric acid, sulfuric acid and phosphoric acid. The mineral acid is used in an amount of 1.0 to 5.0 equivalents per equivalent of the basic catalyst used in the synthesis of the amidonitrile. When the amount of the mineral acid is less than 1.0 equivalent, the neutralization of the basic catalyst will be incomplete to result in a lowered recovery of the amidonitrile, because a fatty acid amide is formed by the function of the unneutralized basic catalyst. On the contrary, when the amount exceeds 5.0 equivalents, the amidonitrile will be decomposed resulting in a lowered recovery. The temperature of the neutralization is preferably about the same as the reaction temperature, though it is not particularly limited.

When the reaction of a lower alkyl ester of a fatty acid represented by the formula (2) with an aminonitrile represented by the formula (3) in the presence of a basic catalyst is conducted either under an elevated pressure with an inert gas or in the coexistence of a lower alcohol added to the reaction system, the obtained aminonitrile represented by the formula (1) can be prevented from undergoing discoloration to reduce or eliminate the above purification step.

Examples of the inert gas include nitrogen gas and argon gas, between which nitrogen gas is preferable. The pressure may be 0.1 kg/cm$^2$ by gauge pressure (hereinafter referred to as "kg/cm$^2$ G") or above, preferably 0.1 to 20 kg/cm$^2$ G. When the pressure is lower than 0.1 kg/cm$^2$ G, no apparent discoloration-inhibiting effect will be attained, while when it exceeds 20 kg/cm$^2$ G, no additional discoloration-inhibiting effect will be attained, but disadvantageously requiring a pressure equipment.

The lower alcohol to be added to the reaction system is an alcohol having 1 to 4 carbon atoms. Examples thereof include methanol, ethanol, 2-propanol and butanol, among which methanol, ethanol and 2-propanol are particularly preferable. When the alkyl group constituting the lower alcohol to be added is the same as that (i.e., $R^4$ in the formula (2)) constituting the lower alkyl ester of a fatty acid represented by the formula (2) to be used as the raw material for the synthesis of the amidonitrile, unreacted part of the ester can be recovered advantageously. The amount of the lower alcohol to be added is preferably 0.01 to 10 times by weight as large as that of the lower alkyl ester of a fatty acid represented by the formula (2). When the amount is less than 0.01 time by weight as large as that of the ester, no apparent discoloration-inhibiting effect will be attained, while when it exceeds 10 times by weight as large as that of the ester, not only is no additional discoloration-inhibiting effect attained, but also the reaction system will be diluted resulting in a lengthened reaction time and a lowered industrial efficiency, disadvantageously. When the boiling point of the lower alcohol used is lower than the reaction temperature, the reaction may be conducted in a hermetically sealed reactor under an elevated pressure.

Further, the above two reaction conditions may be combined in the preparation of the amidonitrile.

When the preparation of an amidonitrile is conducted under the above condition, not only is the obtained amidonitrile remarkably depressed in discoloration but also the yield is enhanced, as compared with the preparation thereof under normal pressure without the addition of any lower alcohol. Accordingly, the amldonitrile can be used in a wide field as the raw material of various reactions.

It is well known that an amide compound can be prepared by reacting a lower alkyl ester of a fatty acid with an amine. Such a reaction is generally conducted with the removal of the lower alcohol formed as a by-product from the reaction system. More specifically, in order to remove out the lower alcohol formed as a by-product from the reaction system, the reaction is conducted either under a reduced pressure or while passing nitrogen gas and the like through the system. When such a condition is applied to the preparation of the amidonitrile, however, a remarkably discolored product is obtained in a lowered yield as compared with the preparation thereof without removing out the lower alcohol from the system. Accordingly, it is preferable in the present invention that the reaction be conducted without removing out the lower alcohol formed as a by-product from the system.

Further, a method which comprises using a fatty acid instead of the lower alkyl ester of a fatty acid represented by the formula (2) is generally known in the preparation of the amidonitrile represented by the formula (1). However, this method cannot be employed in the present invention, because a fatty acid is mixed with the aminonitrile represented by the formula (3) to form an unstable fatty acid salt of amine, which decomposes exothermically (see Comparative Example).

Among the prepared amidonitriles represented by the formula (1), those represented by the formula (1) wherein $R^3$ is a linear or branched alkylene group having 2 to 5 carbon atoms, i.e., those represented by the above formula (1') are novel compounds which have been synthesized by the inventors of the present invention for the first time, and are useful as intermediates for the synthesis of N-(long-chain acyl)amino acids or salts thereof.

h) Preparation Process for N-(long-chain acyl)amino Acid Salt

Reaction formula:

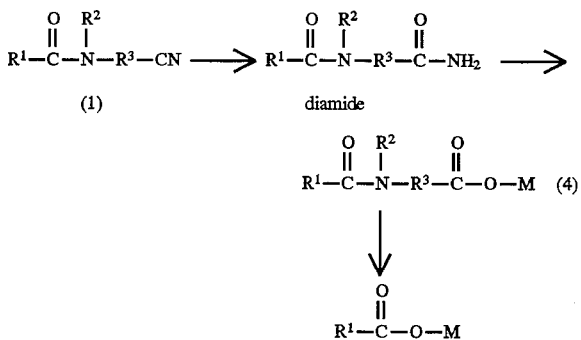

wherein $R^1CO-$, $R^2$, $R^3$ and M are each as defined above.

An N-(long-chain acyl)amino acid salt represented by the above formula (4) can be prepared by hydrolyzing the amidonitrile of the formula (1) prepared by the above process a) in the presence of a basic substance.

N-(Long-chain acyl)amino acid salts represented by the formula (4) wherein $R^2$ is a hydrogen atom or a methyl group and $R^3$ is an ethylene group are preferable, and those represented by the formula (4) wherein $R^2$ is a hydrogen atom and $R^3$ is an ethylene group are particularly preferable. Examples of the monovalent cation, M, include sodium ion, potassium ion and triethanolammonium ion.

The hydrolysis of the amldonitrile represented by the formula (1) must be conducted under such conditions as to hydrolyze only the cyano group, with the amide group being left intact. When an acid is used as the catalyst, formation of the desired N-(long-chain acyl)amino acid salt is difficult, though the formation of a diamide which is an intermediate of the hydrolysis is observed. However, the hydrolysis of the amide group is easily accomplished to remarkably form a long-chain fatty acid. Accordingly, an acidic catalyst cannot be used in the present invention. On the contrary, when a basic substance is used as the catalyst, the disappearance of the amidonitrile is remarkably promoted as compared with the case using an acidic catalyst, though the reason for this phenomenon is not apparent. Further, the amide group is little decomposed. For these reasons, a basic substance is used as the catalyst in the present invention.

It is preferable that the basic substance be one or more members selected from among hydroxides, carbonates and hydrogencarbonates of alkali metals and hydroxides, carbonates and hydrogencarbonates of alkaline earth metals, still preferably sodium hydroxide or potassium hydroxide. The basic substance must be used in an amount of at least 0.9 equivalent per equivalent of the amldonitrile represented by the formula (1). When the amount of the basic substance is less than 0.9 equivalent, an increased amount of a diamide which is an intermediate of the hydrolysis as represented by the above reaction formula, will be contained in the product to lower the purity of the desired N-(long-chain acyl)amino acid salt represented by the formula (4). As long as the amount is 0.9 equivalent or above, the N-(long-chain acyl) amino acid salt represented by the formula (4) can be prepared in a high yield. However, when the basic substance is used in an amount exceeding 2.0 equivalents per equivalent of the amidonitrile represented by the formula (1), the rate of hydrolysis of the amide group in the formed N-(long-chain acyl)amino acid salt represented by the formula (4) will increase, which is causative of lowering in the purity. For these reasons, it is preferable that the basic substance be used in an amount of 0.9 to 2.0 equivalents per equivalent of the amidonitrile represented by the formula (1).

The hydrolysis of the amidonitrile represented by the formula (1) is desirably conducted at a temperature of 60° to 150° C., more desirably 60° to 110° C., most desirably 80° to 110° C. When the temperature is lower than 60° C., the hydrolysis will take a longer time, which is industrially disadvantageous. On the contrary, a higher reaction temperature gives a higher reaction rate. When the temperature is higher than 150° C., however, the pressure of the reaction system will be so enhanced that equipment having a high pressure resistance will be necessitated. Accordingly, it is still preferable from the standpoint of the balance between both tendencies that the reaction temperature ranges from 80° to 110° C. By satisfying these requirements, a high-quality aqueous solution of an N-(long-chain acyl)amino acid salt represented by the formula (4) can be prepared industrially advantageously.

The N-(long-chain acyl)amino acid salt thus prepared can be used as such in some fields. However, the aqueous solution of the N-(long-chain acyl)amino acid salt which is prepared according to the present invention contains a lower alcohol resulting from the lower alkyl ester of a fatty acid used as the raw material and/or ammonia formed during the hydrolysis of the amidonitrile, so that it is desirable that the aqueous solution be separated from these components prior to the use thereof. Examples of the method for removing these components include removals through heat distillation and steam distillation, though it is not particularly limited. Further, a product having a higher purity can be obtained by the conventional purification means such as column chromatography, solvent washing and the like.

It is preferable in order to prepare an N-(long-chain acyl)amino acid salt represented by the formula (4) at a higher purity that the amidonitrile of the formula (1) used as the raw material be one prepared by the removal of the basic catalyst used for the synthesis thereof and distillation, or one prepared by reacting a lower alkyl ester of a fatty acid represented by the formula (2) with an aminonitrile represented by the formula (3) in the presence of a basic catalyst, either under an elevated pressure with an inert gas or in the coexistence of a lower alcohol added, as described above.

c) Preparation Process for N-(long-chain acyl)amino Acid

An N-(long-chain acyl)amino acid represented by the formula (5) can be prepared by adjusting the pH of the above-prepared aqueous solution of an N-(long-chain acyl) amino acid salt represented by the formula (4) to a pH from 1 to 5 with a mineral acid to form an N-(long-chain acyl)amino acid, and separating and recovering the N-(long-chain acyl)amino acid.

N-(Long-chain acyl)amino acids represented by the formula (5) wherein $R^2$ is a hydrogen atom or a methyl group and $R^3$ is an ethylene group are preferable, and those represented by the formula (5) wherein $R^2$ is a hydrogen atom and $R^3$ is an ethylene group are particularly preferable.

It is not particularly difficult to convert an N-(long-chain acyl)amino acid salt represented by the formula (4) into an N-(long-chain acyl)amino acid represented by the formula (5). For example, the convension can be conducted by adjusting the pH of the aqueous solution of an N-(long-chain acyl)amino acid salt represented by the formula (4) to a pH from 1 to 5 with a mineral acid such as sulfuric acid, hydrochloric acid and phosphoric acid. More specifically, the conversion can be conducted by adding a mineral acid to the aqueous solution containing an N-(long-chain acyl) amino acid salt under stirring to adjust the pH of the solution to a pH from 1 to 5. The temperature of the conversion is not particularly limited.

The N-(long-chain acyl)amino acid thus formed can be separated and recovered by crystallization or the like. However, the recovery of a crystal by filtration is disadvantageous in that special equipment is necessitated and much water is necessary to wash off impurities contained in the crystal. Therefore, it is particularly preferable that the N-(long-chain acyl)amino acid be separated and recovered by the phase-separation technique which comprises separating the reaction mixture into an aqueous phase and an organic phase containing an N-(long-chain acyl)amino acid by heating the reaction mixture to bring the N-(long-chain acyl)amino acid into a fused (or molten) state, recovering the organic phase, and then recovering the N-(long-chain acyl) amino acid therefrom. The term "fused (or molten) state" used with respect to N-(long-chain acyl)amino acid refers to a liquidized state exhibiting fluidity.

The temperature at which the reaction mixture is separated into an aqueous phase and an organic phase containing an N-(long-chain acyl)amino acid generally ranges from room temperature to 100° C., though the temperature may be any one at which the (N-long-chain acyl)amino acid is fused (or melted). When the temperature exceeds 100° C., the phase-separation will have to be conducted under pressure because the temperature exceeds the boiling point of water, thus necessitating much equipment the cost of which is disadvantageous. Although the phase-separation can, of course, be conducted at a temperature above the melting point of the N-(long-chain acyl)amino acid, it can be conducted even at a relatively low temperature advantageously, because the N-(long-chain acyl)amino acid is fused at a temperature below its melting point when it contains water. Although, in general, a mixture of a molten N-(long-chain acyl)amino acid with water is ready separated when left to stand, this tendency, even if low in some cases, can be enhanced by the addition of an inorganic salt such as sodium sulfate and sodium chloride. After the phase-separation, the aqueous phase was separated to thereby obtain a water-containing N-(long-chain acyl)amino acid. In order to enhance the purity, the above phase-separation may be repeated two or more times. Further, the phase-separation may be conducted by any of batch-wise and continuous processes.

It is not particularly difficult to dry the water-containing N-(long-chain acyl)amino acid prepared by the above phase-separation technique. Examples of the method for the drying includes drying by vacuum heating, drying by passing a gas such as air and nitrogen through the system, drying by solidifying through cooling followed by pulverizing, and spray drying.

Further, the water-containing N-(long-chain acyl)amino acid prepared by the above phase-separation technique can as such be used, when the use of a dry N-(long-chain acyl)amino acid is not particularly required, for example, when use is made of an aqueous solution of an N-(long-chain acyl)amino acid salt different from that prepared by the above preparation process for N-(long-chain acyl)amino acid salt. Further, the water-containing N-(long-chain acyl) amino acid may be as such granulated by spray cooling, tumbling granulation or the like.

The N-(long-chain acyl)amino acid of the formula (5) prepared by the above process of the present invention is usable in various fields including surfactants, either as such, or in a state converted into an inorganic or organic salt by a conventional manner at need.

According to the process of the present invention, a high-quality N-(long-chain acyl)amino acid or salt thereof which is extremely useful as a low irritation surfactant or the like can be prepared from inexpensive raw materials industrially advantageously.

Further, the present invention also provides a novel amidonitrile which is useful as an intermediate in the synthesis of an N-(long-chain acyl)amino acid or a salt thereof, and a process for the preparation thereof.

EXAMPLES

The present invention will now be described by referring to the following Examples in detail, though the present invention is not limited by them.

In the Examples, all percentages are by weight, unless otherwise noted.

Examples on the Preparation of Amidonitrile

Examples 1 to 7

1072 g (5 mol) of methyl laurate was put in a 5-l four-necked, round-bottomed flask fitted with a stirrer, a condenser and a thermometer, followed by stirring. Oxygen in the reactor was purged with nitrogen, followed by the addition of 350 g (5 mol) of β-aminopropionitrile and a 28% solution of sodium methylate in methanol in this order. The temperature of the obtained mixture was raised to a predetermined temperature and the mixture was subjected to the reaction or aging at that temperature to give the desired amidonitrile, i.e., N-lauroyl-β-aminopropionitrile. The same procedure as described above was repeated except that the amount of the 28% solution of sodium methylate in methanol used and the reaction or aging temperature were varied. Thus, the influences of the amount of the 28% solution (i.e., the amount of catalyst) and the reaction temperature on the yield of the amldonitrile were determined. The results are given in Table 1.

The amount of the amidonitrile was determined by liquid chromatography and the molar yield based on β-aminopropionitrile is given in the Table 1.

TABLE 1

| Ex. No. | Amt. of catalyst (g) | mole %* | React. aging temp. (°C.) | React. aging time (hr) | Yield (%) | Remarks |
|---|---|---|---|---|---|---|
| 1 | 9.6 | 1.0 | 90 | 40 | 60 | |
| 2 | 48.0 | 5.0 | 70 | 40 | 60 | 10%** of methanol added |
| 3 | 48.0 | 5.0 | 90 | 6 | 90 | |
| 4 | 48.0 | 5.0 | 120 | 1 | 80 | |
| 5 | 48.0 | 5.0 | 150 | 1 | 50 | |
| 6 | 96.0 | 10.0 | 90 | 4 | 90 | |
| 7 | 192.0 | 20.0 | 90 | 2 | 90 | | note)
*: mole % based on β-aminopropionitrile
**: wt. % based on the %weight of methyl laurate The N-lauroyl-β-aminopropionitrile prepared in the Example 3 was recrystallized from methanol and the melting point, IR spectrum and NMR spectrum of the resulting N-lauroyl-β-aminopropionitrile are as follows:

m.p.: 96° to 97° C.

IR: 3290 cm$^{-1}$ (N-H)

$\left.\begin{array}{l}3090\ \text{cm}^{-1}\\ 2930\ \text{cm}^{-1}\\ 2850\ \text{cm}^{-1}\end{array}\right\}$ (C—H)

2250 cm$^{-1}$ (C≡N)

1650 cm$^{-1}$ (C=O)

NMR: δ 1.0(3H, t, C$\underline{H_3}$—)   a 1.4(16H, m, —C$\underline{H_2}$—)   b 1.8(2H, m, —C$\underline{H_2}$—CH$_2$—C—)   c
         O
         ‖

2.3(2H, t, —C$\underline{H_2}$—C—)   d
              O
              ‖

2.7 (2H, t, —C$\underline{H_2}$—C≡N)   g 3.6 (2H, q, NH—C$\underline{H_2}$—)   f 6.1(1H, m, —NH—)   e

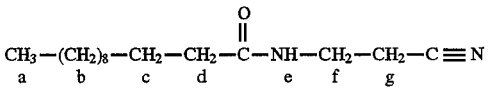

Comparative Example 1

100.0 g (0.5 mol) of lauric acid previously stirred was put In a 500-ml four-necked, round-bottomed flask fitted with a stirrer, a condenser and a thermometer, followed by stirring at 50° C. Oxygen in the reactor was purged with nitrogen, followed by the addition of 35.0 g (0.5 mol) of β-aminopropionitrile. The temperature of the obtained mixture was raised. In the course of the temperature-raising step, the reaction mixture emitted white smoke at about 60° C. exothermically. After 5 minutes therefrom, the bulk temperature of the flask reached 130° C. and the contents of the flask were in the form of a reddish-black tar. The amount of N-lauroyl-β-aminopropionitrile was determined by liquid chromatography. The yield was 5 mole % or below.

Examples 8 to 11

Phosphoric acid was added to the N-lauroyl-β-aminopropionitrile (purity: 78%) prepared in the Example 3 at 90° C. to conduct neutralization. The resulting mixture was vacuum-filtered. The obtained catalyst-free filtrate containing N-lauroyl-β-aminopropionitrile was distilled in a vacuum. This distillation was conducted with a glass-made batch distillator under the conditions of 0.5 to 1.0 mmHg and 180° to 220° C. The amount of the N-lauroyl-β-aminopropionitrile contained in the distillate thus obtained was determined to calculate the recovery thereof based on the amount of N-lauroyl-β-aminopropionitrile before the neutralization.

The same procedure as described above was repeated except that the amount of the phosphoric acid added was varied, by which the influence of the amount of the phosphoric acid added on the recovery of N-lauroyl-β-aminopropionitrile was determined. The results are given in Table 2.

TABLE 2

| Ex. No. | Amt. of* phosphoric acid added (equiv.) | Recovery (%) | Purity of distillate (%) |
|---|---|---|---|
| 8 | 1 | 80 | 90 |
| 9 | 3 | 90 | 95 |
| 10 | 5 | 90 | 95 |
| 11 | 10 | 70 | 80 | note)
*: equivalent of phosphoric acid based on sodium methylate used in Ex. 3

Examples 12 to 14

214.3 g (1 mol) of methyl laurate, 70 g (1.0 mol) of β-aminopropionitrile and 9.6 g of a 28% solution of sodium methylate in methanol were fed into a 1-l autoclave. Oxygen in the reactor was purged with nitrogen, and then the system was pressurized with nitrogen up to a predetermined pressure at room temperature. The temperature of the contents was raised to 90° C. under such conditions and the reaction or aging was effected for 6 hours. After the completion of the reaction, the amount of N-lauroyl-β-aminopropionitrile was determined by liquid chromatography to calculate the molar yield thereof based on β-aminopropionitrile. Further, 3 g of the N-lauroyl-β-aminopropionitrile was dissolved in 17 g of dimethylformamide containing 10% of water and the obtained solution was examined for hue.

The same procedure as described above was repeated except that the reaction pressure was varied. Thus, the influences of the pressure on the yield and hue of N-lauroyl-β-aminopropionitrile were determined. The results are given in Table 3.

Examples 15 to 17

214.3 g (1 mol) of methyl laurate, 70 g (1.0 mol) of β-aminopropionitrile, 9.6 g of a 28% solution of sodium methylate in methanol and a predetermined amount of methanol were fed into a 1-l autoclave. At room temperature, oxygen in the autoclave was purged with nitrogen, and then the autoclave was hermetically sealed. The temperature of the contents was raised to 90° C. under such conditions and the reaction or aging was effected for 8 hours. After the completion of the reaction, the amount of N-lauroyl-β-aminopropionitrile was determined by liquid chromatography to calculate the molar yield thereof based on β-aminopropionitrile. Further, 3.0 g of the N-lauroyl-β-aminopropionitrile was dissolved in 17 g of dimethylformamide containing 10% of water and the obtained solution was examined for hue.

The same procedure as described above was repeated except that the amount of methanol added was varied. Thus, the influences of the amount of methanol added on the yield and hue of N-lauroyl-β-aminopropionitrile were determined. The results are given in Table 3.

Example 18

214.3 g (1 mol) of methyl laurate, 70 g (1.0 mol) of β-aminopropionitrile, 9.6 g of a 28% solution of sodium methylate in methanol and 21.4 g of methanol were fed into a 1-l autoclave. At room temperature, oxygen in the autoclave was purged with nitrogen, and then the system was pressurized to 1.0 kg/cm² G with nitrogen. The temperature of the contents was raised to 90° C. under such conditions and the reaction or aging was effected for 8 hours. After the completion of the reaction, the yield and hue of the obtained N-lauroyl-β-aminopropionitrile were determined. The results are given in the Table 3.

Example A 214.3 g (1 mol) of methyl laurate, 70 g (1.0 mol) of β-aminopropionitrile and 9.6 g of a 28% solution of sodium methylate in methanol were put in a 1-l four-necked flask fitted with a stirrer, a condenser and a thermometer. Oxygen in the reactor was purged with nitrogen at room temperature. The temperature of the contents was raised to 90° C. under such conditions and the reaction or aging was effected for 6 hours. After the completion of the reaction, the yield and hue of the obtained N-lauroyl-β-aminopropionitrile were determined. The results are given in the Table 3.

Example B 214.3 g (1 mol) of methyl laurate, 70 g (1.0 mol) of β-aminopropionitrile and 9.6 g of a 284 solution of sodium methylate in methanol were put in a 1-l four-necked flask. Oxygen in the reactor was purged with nitrogen at room temperature. The reaction or aging was effected under a reduced pressure of 200 mmHg at 90° C. for 6 hours. After the completion of the reaction, the yield and hue of the obtained N-lauroyl-β-aminopropionitrile were determined. The results are given in the Table 3.

TABLE 3

| | Pressure*¹ | Amt. of*² methanol added | Yield (%) | Hue |
|---|---|---|---|---|
| Ex. | | | | |
| 12 | 0.2 kg/cm² G | 0 | 92 | Gardner 2 |
| 13 | 1.0 kg/cm² G | 0 | 94 | Gardner 2 |
| 14 | 5.0 kg/cm² G | 0 | 95 | Gardner 1 |
| 15 | normal | 0.1 | 90 | Gardner 1 |
| 16 | normal | 0.5 | 89 | APHA 120 |
| 17 | normal | 1.0 | 87 | APHA 40 |
| 18 | 1.0 kg/cm² G | 0.1 | 92 | APHA 120 |
| Ex. | | | | |
| A | normal | 0 | 90 | Gardner 8 |
| B | 200 mmHg | 0 | 61 | Gardner 14 | note)
*¹: pressure before temperature rise (at room temp.)
*²: weight ratio of methanol to methyl laurate

Examples on the Preparation of N-(long-chain acyl)-amino Acid Salt

Example 19

49.2 g (0.15 mol) of the N-lauroyl-β-aminopropionitrile (purity: 78%) prepared in the Example 3, 36 g of deionized water and 50.5 g (0.18 mol) of a 20% aqueous solution of potassium hydroxide were fed into a 500-ml four-necked, round-bottomed flask fitted with a stirrer, a condenser and a thermometer, and the reaction was effected at 90° C. for 15 hours. Thus, a 32.4% aqueous solution of potassium N-lauroyl-β-alaninate was obtained. The conversion of N-lauroyl-β-aminopropionitrile into potassium N-lauroyl-β-alaninate was 95 mole %. The aqueous solution had a hue of 5 on the Gardner color scale.

Example 20

39.9 g (0.15 mol) of the distilled N-lauroyl-β-aminopropionitrile (purity: 95%) prepared in the Example 9, 43.2 g of deionized water and 50.5 g (0.18 mol) of a 20% aqueous solution of potassium hydroxide were fed into a 500-ml four-necked, round-bottomed flask fitted with a stirrer, a condenser and a thermometer, and the reaction was effected at 90° C. for 15 hours. Thus, a 33% aqueous solution of potassium N-lauroyl-β-alaninate was obtained. The conversion of N-lauroyl-β-aminopropionitrile into potassium N-lauroyl-β-alaninate was 95 mole % and the yield of potassium laurate was 2 mole %. The aqueous solution had a hue of 50 on the APHA scale.

Example 21

The same procedure as that of the Example 20 was repeated except that a 204 aqueous solution of sodium hydroxide was used instead of the 20%aqueous solution of potassium hydroxide. The conversion of N-lauroyl-β-aminopropionitrile into sodium N-lauroyl-β-alaninate was 95 mole %. The yield of sodium laurate was 2 mole %.

Example 22

46.8 g (0.15 mol) of the N-lauroyl-β-amino-propionitrile (purity: 81%) prepared in the Example 13, 38.4 g of deionized water and 50.5 g (0.18 mol) of a 20% aqueous solution of potassium hydroxide were fed into a 500-ml four-necked, round-bottomed flask fitted with a stirrer, a condenser and a thermometer, and the reaction was effected at 90° C. for 15 hours. Thus, a 32.84 aqueous solution of potassium N-lauroyl-β-alaninate was obtained. The conversion of N-lauroyl-β-aminopropionitrile into potassium N-lauroyl-β-alaninate was 96 mole %. The aqueous solution had a hue of 1 on the Gardner color scale.

Example 23

67.6 g (0.15 mol) of the N-lauroyl-β-aminopropionitrile (purity: 56%) prepared in the Example 16, 17.6 g of deionized water and 50.5 g (0.18 mol) of a 20% aqueous solution of potassium hydroxide were fed into a 500-ml four-necked, round-bottomed flask fitted with a stirrer, a condenser and a thermometer, and the reaction was effected at 90° C. for 15 hours. Thus, a 32.5% aqueous solution of potassium N-lauroyl-β-alaninate was obtained. The conversion of N-lauroyl-β-aminopropionitrile into potassium N-lauroyl-β-alaninate was 95 mole %. The aqueous solution had a hue of 80 on the APHA scale.

Example 24

39.9 g (0.15 mol) of the distilled N-lauroyl-β-aminopropionitrile (purity: 95%) prepared in the Example 9, 43.2 g of deionized water and 50.5 g (0.18 mol) of a 20% aqueous solution of potassium hydroxide were fed into a 500-ml autoclave, and the reaction was effected at 120° C. for 5 hours. Thus, a 32.8% aqueous solution of potassium N-lauroyl-β-alaninate was obtained. The conversion of N-lauroyl-β-aminopropionitrile into potassium N-lauroyl-β-alaninate was 95 mole %. The yield of potassium laurate was 2 mole %.

Comparative Example 2

39.9 g (0.15 mol) of the distilled N-lauroyl-β-aminopropionitrile (purity: 95%) prepared in the Example 9, 72.2 g of deionized water and 22.5 g (0.23 mol) of 98% sulfuric acid were fed into a 500-ml four-necked, round-bottomed flask fitted with a stirrer, a condenser and a thermometer, and the reaction was effected at 90° C. for 15 hours. No N-lauroyl-β-alanine was detected in the obtained reaction mixture. Unreacted N-lauroyl-β-aminopropionitrile was contained in the reaction mixture in an amount of 82 mole % of the feed and a diamide and lauric acid formed as by-products were detected in amounts of 6 and 7 mole %, respectively.

Comparative Example 3

The same procedure as that of the Comparative Example 2 was repeated except that 24.0 g (0.23 mol) of 35% hydrochloric acid was used instead of the 98% sulfuric acid. No N-lauroyl-β-alanine was detected in the reaction mixture. Unreacted N-lauroyl-β-aminopropionitrile was contained in the reaction mixture in an amount of 58% of the feed and a diamide and lauric acid formed as by-products were detected in amounts of 16 and 18 mole %, respectively.

Examples on the Preparation of N-(long-chain acyl) -amino Acid

Example 25

100 g of the 88% aqueous solution of potassium N-lauroyl-β-alaninate prepared in the Example 20 was fed into a 500-ml four-necked, round-bottomed flask fitted with a stirrer, a condenser and a thermometer, followed by the dropwise addition of 24.5 g (0.24 mol) of 35% hydrochloric acid in one hour at 70° C. The obtained mixture was subjected to the reaction or aging at that temperature for one hour. After the completion of the reaction or aging, the reaction mixture was vacuum-filtered. The obtained filter cake was washed with 100 g of warm water of 70° C. and vacuum-dried. The yield of the crystal thus obtained was 29 g. This crystal had a whiteness of 98% and a purity of 92% and contaminated by 6% of lauric acid.

The term "whiteness" refers to a color difference between a sample and a standard white plate as determined with SZ-Σ80 mfd. by Nippon Denshoku Kogyo K.K.

Example 26

100 g of the 38% aqueous solution of potassium N-lauroyl-β-alaninate prepared in the Example 20 was fed into a 500-ml four-necked, round-bottomed flask fitted with a stirrer, a condenser and a thermometer, followed by the dropwise addition of 24.5 g (0.24 mol) of 354 hydrochloric acid in one hour at 70° C. The obtained mixture was subjected to the reaction or aging at that temperature for one hour to give a slurry containing crystalline N-lauroyl-β-alanine. The temperature of this slurry was raised to 85° C. to melt the crystalline N-lauroyl-β-alanine. The resulting slurry was allowed to stand at 90° C. for 15 minutes to be separated into an organic phase and an aqueous phase. The organic phase was recovered, by which 33 g of water-containing N-lauroyl-β-alanine was obtained. This water-containing N-lauroyl-β-alanine was dried by vacuum heating (120° C., 200 mmHg) to give 29 g of N-lauroyl-β-alanine.

The obtained N-lauroyl-β-alanine had a whiteness of 934 and a purity of 964 and contaminated by 4% of lauric acid.

Comparative Example 4 (Schotten-Baumann process)

98 g of β-alanine was dissolved in 399 g of deionized water. 129 g of a 484 aqueous solution of potassium hydroxide was added to the obtained solution to form an aqueous solution of potassium β-alaninate. Then, 219 g of lauroyl chloride was added to this aqueous solution in about 1.5 hours, while the pH of the resulting mixture was maintained to about 11.5 with 187 g of a 304 aqueous solution of potassium hydroxide. After the completion of the addition of the lauroyl chloride, the obtained mixture was stirred at 50° C. for one hour to form 1032 g of a 28.54 aqueous solution of potassium lauroyl-β-alaninate. The pH of the aqueous solution thus obtained was adjusted to 1 with 354 hydrochloric acid to precipitate lauroyl-β-alanine. The resulting mixture was vacuum-filtered and the obtained filter cake, i.e., lauroyl-β-alanine, was washed with 1000 g of warm water of 70° C. and vacuum-dried. The yield of the crystal thus obtained was 267 g. This crystal had a whiteness of 92% and a purity of 92% and contaminated by 7% of lauric acid, thus being equivalent to the product of the Example 25 in quality.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for the preparation of an amidonitrile represented by the following formula (1):

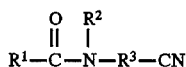

wherein $R^1CO-$ represents a saturated or unsaturated fatty acid residue having 8 to 22 carbon atoms; $R^2$ represents a hydrogen atom or a linear or branched alkyl group having 1 to 3 carbon atoms; and $R^3$ represents ethylene, which comprises a step of reacting a lower alkyl ester of a fatty acid represented by the following formula (2):

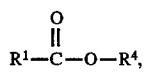 (2)

wherein $R^1CO-$ is as defined above; and $R^4$ represents an alkyl group having 1 to 4 carbon atoms, with an aminonitrile represented by the formula (3):

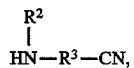 (3)

wherein $R^2$ and $R^3$ are each as defined above, in the presence of a basic catalyst which is an alkali or alkaline earth metal alcoholate having 1 to 3 carbon atoms.

2. The process for the preparation of an amidonitrile as set forth in claim 1, wherein $R^2$ is a hydrogen atom or a methyl group.

3. The process for the preparation of an amidonitrile as set forth in claim 1, wherein the reaction is conducted without removing out the lower alcohol formed as a by-product from the reaction system.

4. The process for the preparation of an amidonitrile as set forth in claim 1, which further comprises the steps of removing out the basic catalyst from the reaction mixture and purifying the reaction product by distillation.

5. The process for the preparation of an amidonitrile as set forth in claim 4, wherein the removal of the basic catalyst is conducted by neutralizing the basic catalyst with a mineral acid and removing the salt formed.

6. The process for the preparation of an amidonitrile as set forth in claim 1, wherein the reaction of a lower alkyl ester of a fatty acid represented by the formula (2) with an aminonitrile represented by the formula (3) is conducted in the presence of an inert gas under an elevated pressure.

7. The process for the preparation of an amidonitrile as set forth in claim 6, wherein the elevated pressure is 0.1 to 20 kg/cm$^2$ gauge.

8. The process for the preparation of an amidonitrile as set forth in claim 1, wherein the reaction of a lower alkyl ester of a fatty acid represented by the formula (2) with an aminonitrile represented by the formula (3) is conducted in the presence of a lower alcohol.

9. The process for the preparation of an amidonitrile as set forth in claim 1, which further comprises the step of adding a lower alcohol before or during the reaction.

10. The process for the preparation of an amidonitrile as set forth in claim 9, wherein the amount of the lower alcohol added is 0.01 to 10 times by weight of the lower alkyl ester of a fatty acid represented by the formula (2).

11. The process for the preparation of an amidonitrile as set forth in claim 9, wherein the lower alcohol is at least one member selected from the group consisting of methanol, ethanol and 2-propanol.

* * * * *